United States Patent [19]

Muncy

[11] Patent Number: 5,295,947
[45] Date of Patent: Mar. 22, 1994

[54] CHIROPRACTIC BRACE

[75] Inventor: Ron Muncy, Lakeland, Fla.

[73] Assignee: H.E. Stanley Laboratories, Winter Haven, Fla.

[21] Appl. No.: 875,324

[22] Filed: Apr. 29, 1992

[51] Int. Cl.⁵ ............................................... A61F 5/00
[52] U.S. Cl. ........................................ 602/5; 602/19
[58] Field of Search .................... 128/869, 889; 602/5, 602/6, 7, 19; 2/44, 92

[56] References Cited

U.S. PATENT DOCUMENTS

| | | |
|---|---|---|
| 2,181,689 | 11/1939 | Bell . |
| 2,285,612 | 6/1942 | Rehthaler . |
| 2,397,709 | 4/1946 | Versoy et al. . |
| 2,813,526 | 11/1957 | Beebe . |
| 3,020,910 | 2/1962 | Ward ................... 128/889 |
| 3,260,261 | 7/1966 | Gallovich ............... 128/889 |
| 3,351,053 | 11/1967 | Stuttle . |
| 3,441,027 | 4/1969 | Lehman . |
| 3,462,775 | 8/1969 | Markwitz ............... 128/889 |
| 3,605,731 | 9/1971 | Tigges . |
| 3,817,245 | 6/1974 | Kroeger ................ 128/889 |
| 4,202,327 | 5/1980 | Glancy ................. 602/19 |
| 4,475,543 | 10/1984 | Brooks et al. . |
| 4,497,315 | 2/1985 | Fettweis et al. . |
| 4,508,110 | 4/1985 | Modglin ................ 602/19 |
| 4,559,933 | 12/1985 | Batard ................. 602/19 |
| 4,574,790 | 3/1986 | Wellershaus . |
| 4,794,916 | 1/1989 | Poterfield .............. 602/19 |
| 4,901,710 | 2/1990 | Meyer . |
| 4,905,678 | 3/1990 | Cumins et al. . |
| 4,957,103 | 9/1990 | Young et al. . |
| 5,012,798 | 5/1991 | Graf et al. . |
| 5,038,760 | 8/1991 | Osborn . |
| 5,048,542 | 9/1991 | Murray ................. 128/889 |
| 5,072,725 | 12/1991 | Miller ................. 602/19 |
| 5,074,288 | 12/1991 | Miller ................. 602/19 |

Primary Examiner—Michael A. Brown
Attorney, Agent, or Firm—Rothwell, Figg, Ernst & Kurz

[57] ABSTRACT

A light weight, substantially rigid chiropractic brace is disclosed which provides support for the lumbar spine area of a human patient while being comfortably worn, even during ambulation. The chiropractic brace is a bi-valve system comprising a posterior support including a recessed portion thereof for aligning the lumbar vertebra and an anterior support including a portion for lifting the patient's abdominal region and locking out any vertical or lateral rocking motions. The chiropractic brace of the present invention also exerts a pelvic tilt to the patient thereby substantially eliminating torque on the lumbar vertebra. The brace aids the body's natural healing process by preventing adverse forces from affecting an injured area.

20 Claims, 4 Drawing Sheets

CHIROPRACTIC BRACE

BACKGROUND OF THE INVENTION

1. Field of the Invention

This invention relates generally to orthopedic supports and braces.

2. Background Art

Lumbar stabilizers or supports of various types have been employed for many years as a device to reduce or control both temporary and chronic discomfort located in the lower back. It is recognized that lumbar insufficiency, in a broad sense, is a failure of the spine to operate as a column to effect proper posture, to permit freedom of movement and to withstand work related loading. These conditions are frequently brought about as a result of weakness of the spine or muscles, inadequate exercise, loss of muscular elasticity or a lack of coordination of the muscles involved.

Lumbar stabilizers for many years have generally assumed the configuration of a corset or belt, often of exaggerated width, which were adapted to encircle a person's body in the lumbar spine area. These devices typically applied uniform pressure over the entire area and were apparently designed to primarily restrict excessive movement or activities of a person employing the device. Thus, such belts normally had little effect other than to restrict a person's activity and mobility to an extent that might tend to preclude an infliction of further damage or bring about extreme discomfort or pain.

For example, one known chiropractic lumbar spine support brace is constructed of elastic bands which laterally wrap around the patient's waist and fasten across the abdominal area via VELCRO or similar fastening structures. Devices of this nature often employ an insert centrally located in the patient's lumbar spine area for providing support to that region. These inserts in some instances may have a vertically disposed central recess which is designed to provide relief for the spinal column and which may be of assistance in seating the insert in an optimum position relative to the lumbar spine area. Other variations of this general configuration include inserts having a firm layer of material cushioned by a softer material, such as foam, proximate the lumbar spine area. In other cases, thermoplastic inserts have been provided which may be heated and contoured to the lumbar spine configuration of each individual patient.

A known lumbar spine support brace of the type described above is illustrated in U.S. Pat. No. 4,475,543. This support brace provides a wide elastic belt with a pouch that is shaped to receive a curing polyurethane foam resin. The belt is strapped on to the patient while the foam resin is curing to a rigid state and the elasticity of the belt acts to shape the resin into conformity with the body region.

Many deficiencies have been recognized with the above-described lumbar spine support braces. For example, the elastic waist wrap structure has a serious shortcoming in that it often times permits slippage resulting in vertical and lateral movement of the brace. Discomfort and pain have also been associated with the elastic wrap caused by pinching or excessive pressure on the skin. Moreover, the inserts utilized to support the lumbar spine area are subject to lateral movement and are shaped such that they fail to effectively eliminate the torque on the lumbar spine.

Thus, there is a great need for improvements in chiropractic lumbar support braces.

SUMMARY OF THE INVENTION

Accordingly, the present invention provides a chiropractic brace for supporting a human spinal column and, particularly the lumbar spine area, comprising a light weight, substantially rigid posterior support means for supporting the posterior region of a human patient including the spinal column area, a light weight, substantially rigid anterior support means for supporting the anterior region of the patient and a closure means for securing the posterior support means and anterior support means around the patient and for locking out lateral and vertical movement of the brace. The closure means also creates a pelvic tilt which substantially eliminates torque on the lumbar spine area. The posterior support means is characterized by providing an alignment means including a recessed portion which, when fastened to the patient, aligns the lumbar spine thereby locking out any means of rotation that could cause damage to this area of the vertebra. The anterior support means is characterized by providing a means for producing a hydrostatic lift to the abdominal area and for preventing both vertical and horizontal rocking motion on the abdominal region.

The chiropractic brace according to the present invention is constructed to prevent both lateral and vertical movement of the brace on the patient and which optimally eliminates the torque on the spine. Also, the brace is light weight and can be worn comfortably by the user both under normal conditions and while exercising or engaging in physical therapy, while still providing optimum support to the spinal column area.

DETAILED DESCRIPTION OF THE PREFERRED EMBODIMENT

Figure 1:
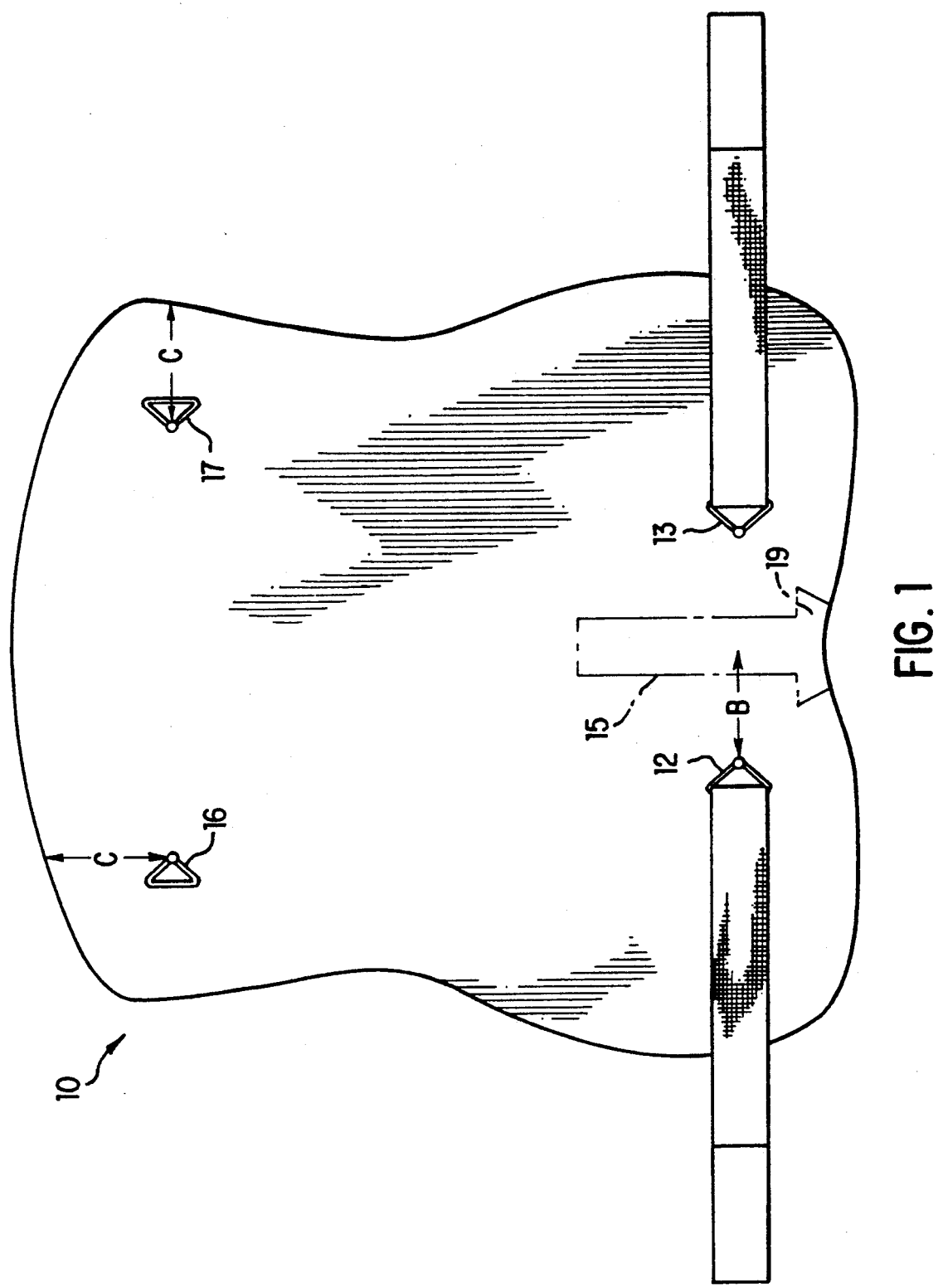
FIG. 1 is a front view illustrating the posterior support means according to the present invention.

A bi-valve chiropractic brace, in accordance with one embodiment of the invention, for supporting the spine area of a human patient will be discussed in detail with reference to FIG. 1 which shows a substantially rigid posterior support means 10 for supporting the posterior region of the patient. Posterior support means 10 comprises an alignment means 15 for aligning at least a portion of the patient's spinal column. The alignment means 15 comprises a recessed portion actually formed into the posterior support means 10 which, when fastened to the patient, aligns and puts pressure on the vertebra. In a preferred embodiment, the recessed portion of the alignment means 15 substantially abuts against the five lumbar vertebra. In a preferred embodiment, the base region of the recessed portion, illustrated at 19 in FIG. 1, flares out to exert pressure on the coccyx area of a human patient.

The recessed portion of the alignment means will have a dimensional depth and area which will enable the targeted vertebra to be aligned. For example, the recessed portion for a chiropractic brace constructed to fit an average adult male has a length of approximately 4 to 6 inches and a width of approximately 1 to 2 inches. In a preferred embodiment, the recessed portion has a length of approximately 5 and one-half inches and a width of approximately 1 and one-half inches. The depth of the recessed portion can be from approximately one-quarter inch to approximately one inch, and in particularly preferred embodiments, approximately one-half inch. The length, width and depth of the recessed portion are otherwise selected for a patient of any size according to the length of the targeted area of the spine, such as the length of the lumbar vertebra.

In the illustrated embodiment, the posterior support means 10 is constructed having a shape which provides the necessary support for the patient, i.e. lumbar spine alignment, preventing rocking motion etc., and which is also more comfortable for the patient. A top portion of the posterior support means supports a substantial portion of the lower back area but does not interfere with the scapula nor impinge on its bony prominent. This configuration permits freedom of movement without pain or discomfort caused by the brace. A bottom portion of the posterior support means rests just above the buttocks of the patient. In a preferred embodiment, the vertical length of the posterior support means, for an average male adult, is approximately 10 to 12 inches and, in a preferred embodiment, 10 and one-half inches. The present design allows substantial freedom of movement for the patient while preventing re-injury during the healing process.

Figure 2:
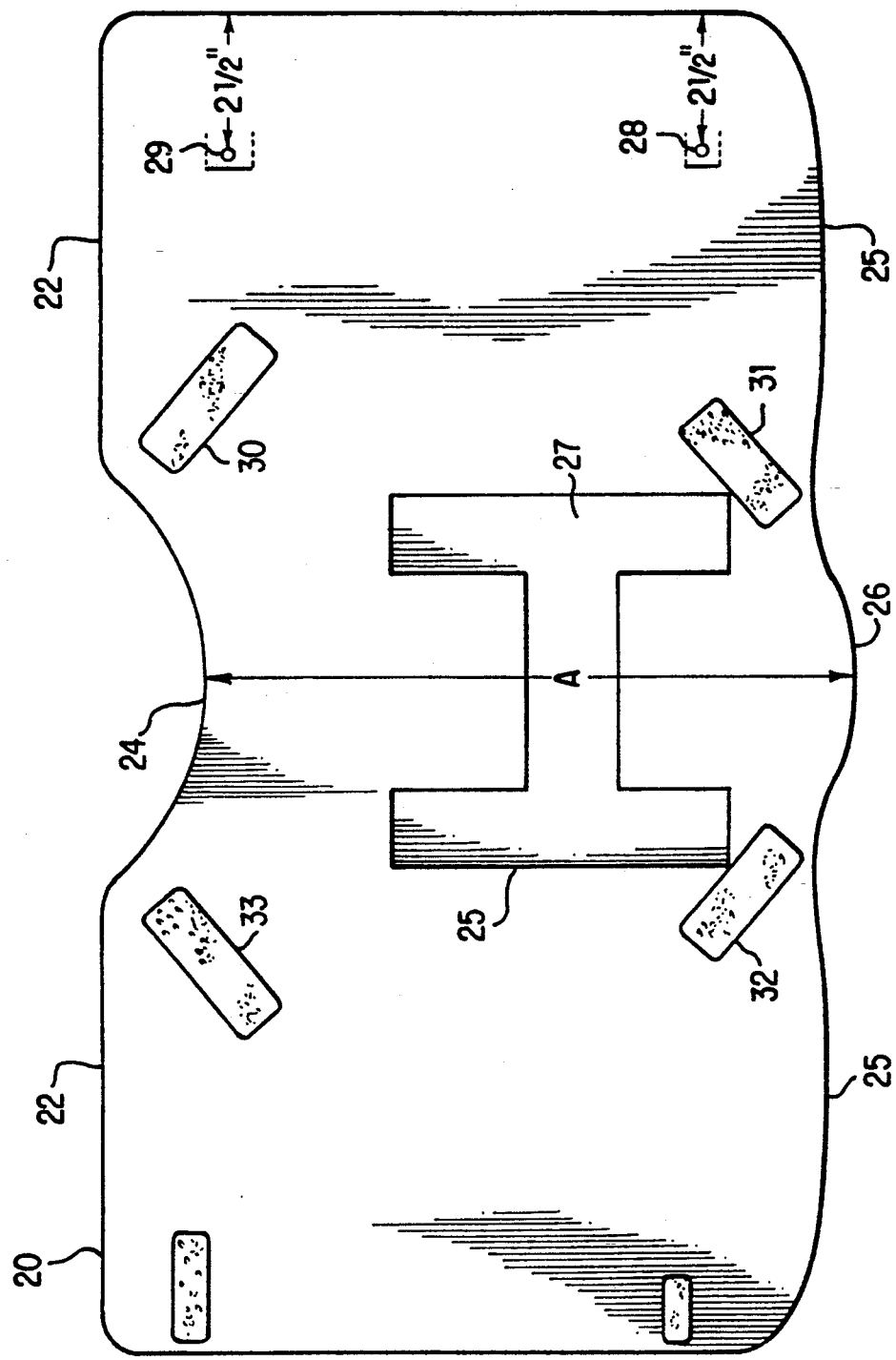
FIG. 2 is a front view of the anterior support means according to the present invention.

The chiropractic brace of the present invention also comprises a substantially rigid anterior support means 20, one embodiment of which is illustrated in FIG. 2, for supporting the anterior region of the patient. Anterior support means 20 comprises a lift means 25 for adding strength to the abdominal area and for providing lift to the abdominal wall of the patient. Lift means 25 comprises a recessed potion 27 which, when fastened, contacts the patient's abdominal region providing support and lift thereto. Providing hydrostatic lift to the abdominal area is an important feature because it prevents the negative forces of gravity causing twisting, turning and poor posture. The means for providing hydrostatic lift provides vertical support for the abdominal region and restricts lateral movement thereof. In a preferred embodiment, the recessed portion 27 of the lift means 25 is substantially H-shaped, as shown in FIG. 2. The H-shaped recessed portion 27 not only provides abdominal lift to the patient, but also prevents both lateral and vertical rocking motions on the abdominal region. In particular, the central, horizontal portion of the H-shaped recess holds the abdominal wall up and the vertical side portions prevent the rocking motion. The H-shaped recessed portion holds the abdominal wall substantially completely static.

The lift means 25 is formed having any suitable size which will effectuate the lifting function on the abdominal wall. In one embodiment, the recessed portion 27 is approximately three to six inches in vertical length and, in preferred embodiments, approximately four inches. Recessed portion 27 is also approximately four to seven inches in horizontal length and, preferably, approximately five inches in length. The recessed portion 27 has a depth of approximately one-quarter inch to approximately one inch and, preferably, approximately one-half inch.

In the illustrated embodiment, the anterior support means 20 is not only constructed to support the lumbar vertebra and facilitate the healing process, but is also shaped to more comfortably facilitate ambulation. A top portion 22 of anterior support means 20 encases the rib cage thereby avoiding possible irritation and discomfort caused by other known braces which impinge or dig into the ribs themselves. The top portion of the support means also has a recessed portion 24 which exposes the xyphoid process for increased patient comfort. A bottom portion 25 of the anterior support means generally extends just below the patient's hip bones and portion 26 extends to approximately just above the patient's pubis bone. In one embodiment of the present invention, the vertical length of the anterior support means from portions 24 to 26, illustrated in FIG. 2 as distance "A", is approximately seven to nine inches and, in more preferred embodiments, approximately eight inches. Also, the vertical length from portions 22 to 25 is approximately six and one-half to eight and one-half inches and, in more preferred embodiments, approximately seven and one-half inches.

Another important feature of the present invention is that both the posterior support means 10 and the anterior support means 20, FIG. 2, are constructed of a substantially rigid, light weight material. For example, the posterior and anterior support means can be made of any suitable light weight material which is rigid but allows for flexing, such as kydex, a form of PVC. The posterior and anterior support means can be constructed by any suitable technique, such as drape forming over a form, and in accordance with one embodiment, approximately 1/16" thick. An entire chiropractic brace constructed according to the present invention can weigh approximately 14.2 ounces. Constructing a substantially rigid, light weight brace provides greater comfort, is easily worn under clothing, and allows greater ambulation while healing is taking place, over known devices.

Also in accordance with a preferred embodiment, the posterior and anterior support means are constructed with a relatively thin lining on an interior surface thereof, i.e. adjacent the body, to provide additional comfort to the patient. The thin lining can be any suitable material foam liner. The thin lining can advantageously be approximately ⅛" thick.

The chiropractic brace according to the present invention also comprises a closure means for securing the anterior support means 20 and posterior support means 10 around the patient and for enabling alignment and support of the lumbar vertebra. In the embodiment shown in FIG. 1, the closure means comprises a chafe means for engaging tying straps including bottom chafes 12 and 13 and top chafe 16 and 17. Chafes 12, 13, 16 and 17 are each mounted to the posterior support means 10. In accordance with this embodiment, the closure means also comprises fastening means 30–33, as shown in FIG. 2, for fastening a strap means which is mounted to the anterior support means and engages the chafe means mounted to the posterior support means.

Figure 3:
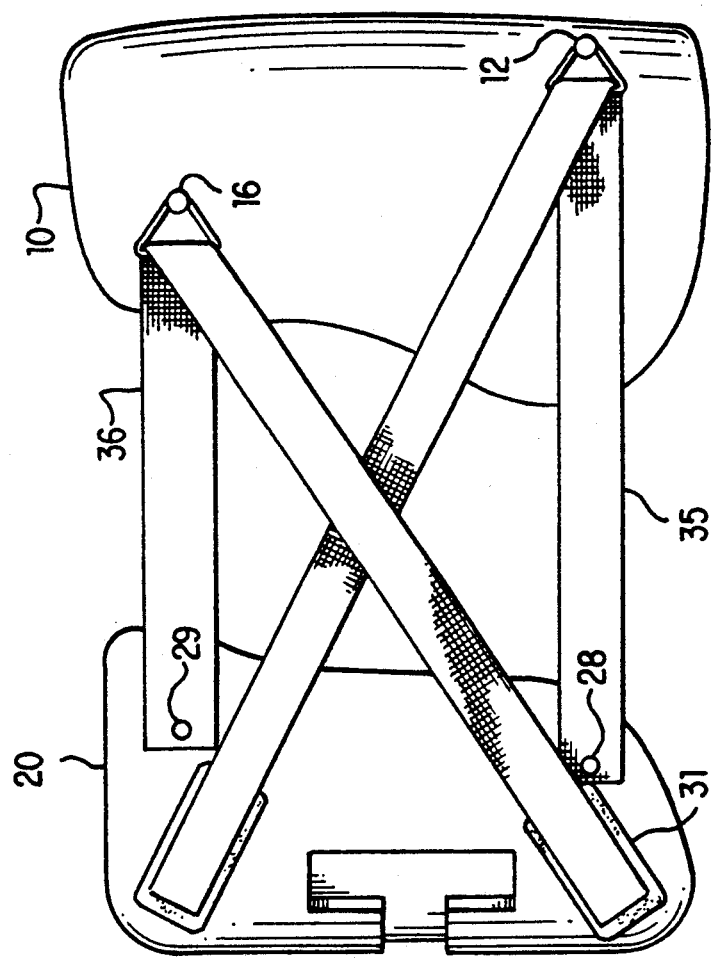
FIG. 3 is a side view of the closure means according to the present invention.

In particular preferred embodiments of the present invention, the closure means is fixed on one side of the brace and adjustable on the other side of the brace, which enables easy donning and doffing for the patient. A fixed closure means is illustrated in FIG. 3, which shows a side view of anterior support means 20 and posterior means 10. Straps 35 and 36 are fixed to anterior support means 20 by a mounting means which can be any suitable mounting structure such as by rivets 28 and 29. The straps 35 and 36 extend across the brace and engage chafe means 12 and 16, respectively, and cross over one another and are fastened to fastening means 30 and 31 respectively. Fastening means 30 and 31 can be any suitable releasably fastening structure such as Velcro hook to be engaged by Velcro pile on the strap ends. Providing one fixed and one adjustable end of the brace allows for more simplified donning and doffing.

Figure 4:
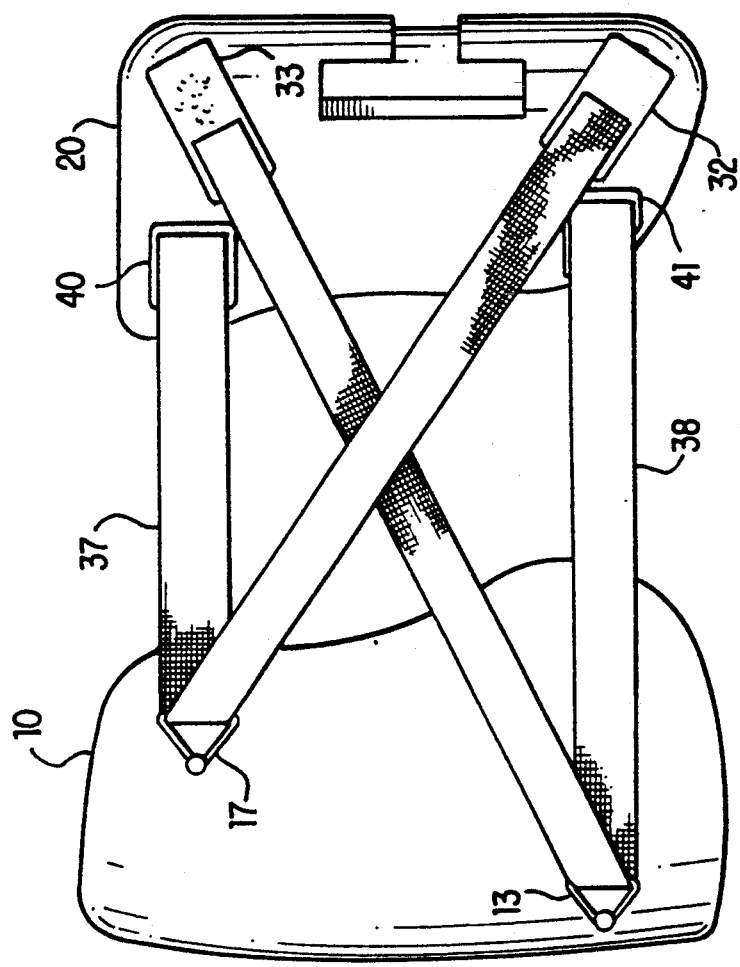
FIG. 4 is an opposite side view of the closure means of FIG. 3.

FIG. 4 illustrates a fully adjustable portion of the closure means which shows a side view of anterior support means 20 and posterior support means 10. Straps 37 and 38 are releasably mounted to the anterior support means 20 by a mounting means which can be any suitable releasable mounting structure, such as Velcro illustrated at 40 and 41. The straps 37 and 38 extend to chafe means 17 and 13, respectively, and cross over one another and are releasably fastened to the anterior support means by fastening means 32 and 33 respectively.

The strap configuration of the closure means, as illustrated in FIGS. 3 and 4, is an important aspect of preferred embodiments of the instant invention. The crisscrossing action of straps 35-36 and 37-38 prevents, migration of brace in the vertical plane of the body once it is applied to the patient. The lateral portion of the strap prevents flexing in and out by the support means and prevents in the lateral plane. The crisscrossing and lateral strap positioning prevents substantially all brace migration. This enables proper support of the spine and improves comfort, even while the patient is engaging in physical therapy.

In the embodiment illustrated in FIGS. 3 and 4, the fixed side of the closure means is mounted on the left side of the brace. It is recognized, however, that the ease of donning and doffing can be accomplished if the fixed side of the closure means is located on the right side of the brace.

Because the patient may have a herniated, bulging, fractured or slipped disk, it is important to eliminate torque on the lumbar spine. The closure means of the present invention also comprises means for providing pelvic tilt to the lumbar spine area which substantially eliminates torque on that region. Referring to FIGS. 1, 3 and 4, straps 35 and 38 run through chafe means 12 and 13, respectively, crossing over and upwards and fastening to fastening means 30 and 33 respectively. The force exerted on the lower portion of posterior support means 10 creates, in combination with alignment means 15, a pull and tilt on the pelvic region thereby aligning and substantially preventing torque on the lumbar vertebra.

Placement of chafe means 12 and 13 is an important element in aligning and substantially eliminating torque on the lumbar spine area. Irrespective of the brace size, the bottom chafe means is mounted a distance, illustrated in FIG. 1 as "B", approximately one to three inches from a vertical plane running through the center of the alignment means. In a preferred embodiment, the chafe means 12 and 13 are mounted two inches from the alignment means center. The chafe means 12 and 13 are also mounted approximately one and one-half to three and one-half inches from the lower edge of posterior support means 10 and, in preferred embodiments, approximately two and one-half inches.

Placement of chafe means 16 and 17 will depend on the size of the chiropractic brace employed i.e. small, medium or large, child or adult. Thus, chafe means 16 and 17 are located a distance, illustrated in FIG. 1 as "C", approximately one to three inches from the outer edge of the posterior support means (horizontal plane) and, in preferred embodiments, approximately two inches.

The chiropractic brace of the present invention enhances support of the lumbar spine area and does not weigh the body muscles down. The inventive brace supports, inter alia, spinal adjustments and facilitates their results. The present invention provides a hydrostatic lift to prevent the negative forces of gravity causing twisting, turning, postural poor work ergonomics. The brace provides these benefits while at the same time not weakening the underlying muscular system and actually facilitating the healing process.

Although the invention has been described in connection with certain embodiments, it is not limited to them. Modifications within the scope of the following claims will be apparent to those skilled in the art without derogating the scope of the applicants, novel contribution to the art.

What is claimed is:

1. A brace for supporting a human spinal column, comprising:
   a) a substantially rigid posterior support means for supporting a posterior region of a human including the spinal column area, said posterior support means comprising an alignment means for aligning an area of the spine, said alignment means comprising a recessed portion in said substantially rigid posterior support means;
   b) a substantially rigid anterior support means for supporting an anterior region of a human, said anterior support means comprising means for producing a hydrostatic lift to an abdominal region of the human, said means for producing hydrostatic lift comprising a recessed portion in said anterior support means; and
   c) closure means for securing said posterior support means and said anterior support means around the human, said closure means comprising means for producing a pelvic tilt on the human so as to substantially prevent torque on a lumbar vertebra area of the human, wherein said recessed portion of said alignment means is positioned on said posterior support means to be abutable against substantially only a lumbar vertebra area of a human.

2. The brace according to claim 1, wherein said closure means comprises a bottom chafe means and a top chafe means mounted to said posterior support means for engaging a strap means, said strap means having an end secured to said anterior support means, said strap means engaging said bottom and top chafe means and having an opposite end secured to said anterior support means.

3. The brace according to claim 2, wherein said chafe means comprises at least a first and a second bottom chafes and at least a first and a second top chafes.

4. The brace according to claim 2, wherein said strap means comprises at least a plurality of straps, said plurality of straps comprising:
   i) a first strap mounted to said anterior support means engaging said first top chafe and releasably secured to said anterior support means;
   ii) a second strap mounted to said anterior support means engaging said first bottom chafe and releasably engaging said anterior support means;

iii) a third strap releasably engaging said anterior support means engaging said second top chafe means and releasably engaging said anterior support means; and iv) a fourth strap releasably engaging said anterior support means engaging said second bottom chafe and releasably fastened to said anterior support means.

5. The brace according to claim 4, wherein said first and second strap crisscross each other and wherein said third and fourth straps crisscross each other.

6. The brace according to claim 2, wherein said means for producing a pelvic tilt comprises said bottom chafe means mounted on said posterior support means a predetermined distance from said alignment means, said strap means engaging said bottom chafe means and being securable to said anterior support means, so as to produce a tilt on a human's pelvic area and substantially prevent torque on a lumbar vertebra area of a human.

7. The chiropractic support brace of claim 6, wherein said predetermined distance that said bottom chafe means is mounted from said alignment means is approximately two inches.

8. The brace according to claim 1, wherein said means for producing a hydrostatic lift comprises a substantially H-shaped recessed portion.

9. The brace according to claim 1, wherein said recessed portion of said lift means provides vertical support for said abdominal region and restricts lateral movement of said abdominal region.

10. The brace according to claim 1, wherein said alignment means is for aligning the lumbar vertebra area of the spine.

11. The brace according to claim 1, wherein said recessed portion of said alignment means is positioned on said posterior support means to be abutable against a lumbar spine area of, a human.

12. The chiropractic support brace of claim 1, wherein said substantially rigid posterior support means and said substantially rigid anterior support means comprise a PVC material.

13. A chiropractic support brace for supporting a human spinal column, comprising:

a) a substantially rigid posterior support means for supporting the posterior region of a human including the spinal column area, said substantially rigid posterior support means having an alignment means for aligning the lumbar spine area of a human, said alignment means comprising a recessed portion in said substantially rigid support means;

b) a substantially rigid anterior support means for supporting an anterior region of the human, said anterior support means comprising means for producing a hydrostatic lift to an abdominal region of the human, said means for producing hydrostatic lift comprising a recessed portion in said anterior support means; and c) closure means mounted to said posterior support means for securing said posterior support means and said anterior support means around the circumference of a human, said closure means comprising a plurality of bottom chafe means mounted to the posterior support means at a predetermined distance from said alignment means and a plurality of top chafe means mounted to said posterior support means at predetermined distance from an outer edge of said posterior support means, said closure means further comprising strap means engaging said bottom and top chafe means for fastening said posterior support means to said anterior support means and for providing lift by said alignment means on the lumbar spine area so as to substantially prevent torque thereon.

14. The chiropractic support brace of claim 13, wherein said recessed portion of said means for providing hydrostatic lift comprises a substantially H-shaped recessed portion.

15. The chiropractic support brace of claim 13, wherein said recessed portion of said alignment means covers substantially the lumbar vertebra area of the spine.

16. The chiropractic support brace of claim 13, wherein said substantially rigid posterior support means and said substantially rigid anterior support means comprises a PVC material.

17. The chiropractic support brace of claim 13, wherein said predetermined distance that said bottom chafe means is mounted from the spine is approximately two inches.

18. The chiropractic support brace of claim 13, wherein said predetermined distance that said top chafe means is mounted to said edge of said posterior support means is approximately two inches.

19. The chiropractic support brace of claim 13, wherein said strap means comprising:

i) a fist strap having a first end and a second end, said first end of said first strap being mounted to a bottom side portion of said anterior support means, said first strap being engagable with one of said plurality of bottom chafe means and securable at said second end to a releasable engaging means on an upper side portion of said anterior support means; and ii) a second strap having a first end and a second end, said first end of said second strap being mounted to a top side portion of said anterior support means, said second strap being engagable with one of said plurality of said top chafe means and securable at said second end to a releasable engaging means on a bottom side portion of said anterior support means.

20. The chiropractic brace according to claim 13, wherein said recessed portion of said lift means is a substantially H-shaped recessed portion.

* * * * *